US011706890B2

(12) United States Patent
Bobgan et al.

(10) Patent No.: US 11,706,890 B2
(45) Date of Patent: Jul. 18, 2023

(54) IMD HAVING A CORE CIRCUITRY SUPPORT STRUCTURE

(71) Applicant: Cardiac Pacemakers, Inc., St. Paul, MN (US)

(72) Inventors: Jean M. Bobgan, Maple Grove, MN (US); David P. Stieper, North Branch, MN (US); Joseph Prescott, St. Paul, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 0 days.

(21) Appl. No.: 17/831,372

(22) Filed: Jun. 2, 2022

(65) Prior Publication Data
US 2022/0295658 A1 Sep. 15, 2022

Related U.S. Application Data

(63) Continuation of application No. 17/132,296, filed on Dec. 23, 2020, now Pat. No. 11,357,125, which is a
(Continued)

(51) Int. Cl.
*H05K 5/00* (2006.01)
*H05K 7/14* (2006.01)
(Continued)

(52) U.S. Cl.
CPC ........... *H05K 7/1427* (2013.01); *A61B 5/021* (2013.01); *A61B 5/1118* (2013.01);
(Continued)

(58) Field of Classification Search
USPC ....... 361/728, 752, 756, 760, 796, 800, 807, 361/809, 810
See application file for complete search history.

(56) References Cited

U.S. PATENT DOCUMENTS 5,173,841 A * 12/1992 Uenaka ................ H05K 7/1417
439/946
5,481,434 A * 1/1996 Banakis ................ G06K 19/18
361/752
(Continued)

FOREIGN PATENT DOCUMENTS

JP 07-045972 A 2/1995
JP 09-162241 A 6/1997
(Continued)

OTHER PUBLICATIONS

International Search Report and Written Opinion issued in PCT/US2017/027895, dated Oct. 10, 2017, 10 pages.
(Continued)

*Primary Examiner* — Hung S. Bui
(74) *Attorney, Agent, or Firm* — Faegre Drinker Biddle & Reath LLP

(57) ABSTRACT

A medical device includes a hybrid circuitry assembly and a core circuitry support structure. The core circuitry support structure includes a frame defining a cavity configured to receive at least a portion of the hybrid circuitry assembly. An outer surface of the frame is shaped to correspond to an inside surface of a core assembly housing configured to enclose the hybrid circuitry assembly and the core circuitry support structure.

15 Claims, 14 Drawing Sheets

Related U.S. Application Data continuation of application No. 16/746,706, filed on Jan. 17, 2020, now Pat. No. 10,881,016, which is a continuation of application No. 16/356,858, filed on Mar. 18, 2019, now Pat. No. 10,542,633, which is a continuation of application No. 15/489,603, filed on Apr. 17, 2017, now Pat. No. 10,237,997.

(60) Provisional application No. 62/324,202, filed on Apr. 18, 2016.

(51) Int. Cl.
*A61B 5/021* (2006.01)
*A61B 5/145* (2006.01)
*A61B 5/11* (2006.01)
*A61B 5/00* (2006.01)
*H05K 5/02* (2006.01)
*A61N 1/375* (2006.01)

(52) U.S. Cl.
CPC ........ *A61B 5/14542* (2013.01); *A61B 5/6847* (2013.01); *A61N 1/3758* (2013.01); *H05K 5/0217* (2013.01)

(56) References Cited

U.S. PATENT DOCUMENTS

| | | |
|---|---|---|
| 5,851,221 A | 12/1998 | Rieder et al. |
| 5,871,514 A | 2/1999 | Wiklund et al. |
| 6,552,911 B1 | 4/2003 | Haupt et al. |
| 6,658,296 B1 | 12/2003 | Wong et al. |
| 7,236,834 B2 | 6/2007 | Christopherson et al. |
| 7,288,736 B2 | 10/2007 | Schildgen |
| 7,349,216 B2 | 3/2008 | Silverbrook et al. |
| 7,414,855 B1 | 8/2008 | Arnold |
| 7,544,220 B2 | 6/2009 | Zhao et al. |
| 8,093,991 B2 | 1/2012 | Stevenson et al. |
| 10,237,997 B2 | 3/2019 | Bobgan et al. |
| 10,327,344 B2 | 6/2019 | Bobgan et al. |
| 10,542,633 B2 | 1/2020 | Bobgan et al. |
| 11,357,125 B2 | 6/2022 | Bobgan et al. |
| 2003/0204216 A1 | 10/2003 | Ries et al. |
| 2003/0204218 A1 | 10/2003 | Vogel et al. |
| 2005/0093928 A1 | 5/2005 | Silverbrook et al. |
| 2005/0137670 A1 | 6/2005 | Christopherson et al. |
| 2006/0047321 A1 | 3/2006 | Biggs et al. |
| 2006/0081570 A1 | 4/2006 | Schildgen |
| 2006/0217778 A1 | 9/2006 | Strom et al. |
| 2006/0222942 A1 | 10/2006 | Zhao et al. |
| 2006/0259091 A1 | 11/2006 | Ries et al. |
| 2007/0016089 A1 | 1/2007 | Fischell et al. |
| 2007/0182715 A1 | 8/2007 | Fyke et al. |
| 2007/0239223 A1 | 10/2007 | Engmark et al. |
| 2008/0303728 A1 | 12/2008 | Lee et al. |
| 2009/0042416 A1 | 2/2009 | Sigg et al. |
| 2009/0059547 A1* | 3/2009 | Maeda ............... H05K 7/142 361/809 |
| 2009/0124965 A1 | 5/2009 | Greenberg et al. |
| 2009/0171420 A1 | 7/2009 | Brown et al. |
| 2010/0048249 A1 | 2/2010 | Furuta et al. |
| 2010/0089634 A1 | 4/2010 | Ahn et al. |
| 2011/0063088 A1 | 3/2011 | Stevenson et al. |
| 2012/0203314 A1* | 8/2012 | Deininger ............ A61N 1/3758 607/115 |
| 2014/0133123 A1 | 5/2014 | Prasannakumar et al. |
| 2014/0207222 A1 | 7/2014 | Knipfer et al. |
| 2015/0157862 A1 | 6/2015 | Greenberg et al. |
| 2016/0061760 A1 | 3/2016 | Nagel et al. |
| 2017/0157405 A1 | 6/2017 | Deininger et al. |
| 2017/0303411 A1 | 10/2017 | Bobgan et al. |
| 2017/0303424 A1 | 10/2017 | Bobgan et al. |
| 2019/0215978 A1 | 7/2019 | Bobgan et al. |
| 2020/0154590 A1 | 5/2020 | Bobgan et al. |
| 2021/0136945 A1 | 5/2021 | Bobgan et al. |

FOREIGN PATENT DOCUMENTS

| | | |
|---|---|---|
| JP | 2008-541443 A | 11/2008 |
| JP | 2010-012236 A | 1/2010 |
| WO | 95/34342 A1 | 12/1995 |
| WO | 02/32503 A1 | 4/2002 |

OTHER PUBLICATIONS

International Search Report and Written Opinion issued in PCT/US2017/028010, dated Oct. 9, 2017, 12 pages.

* cited by examiner

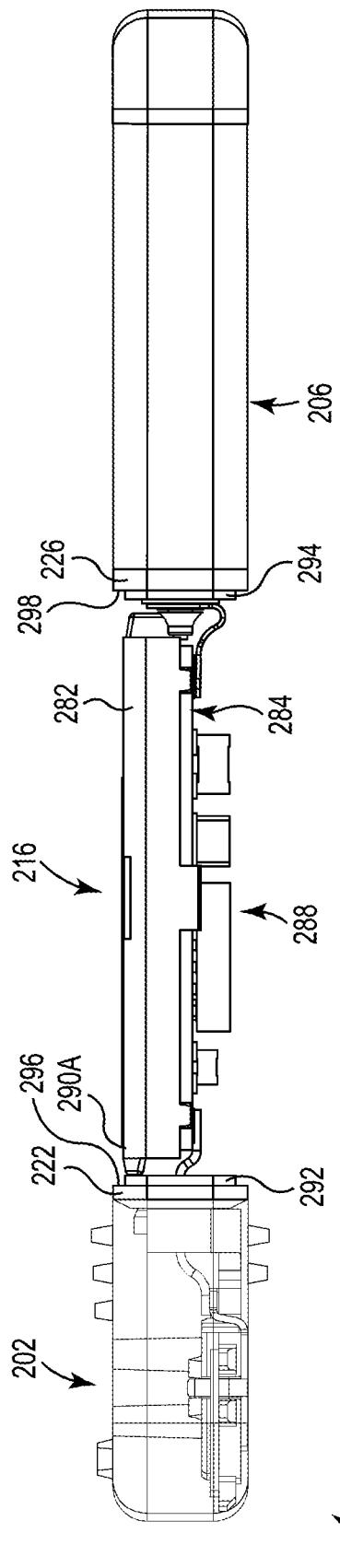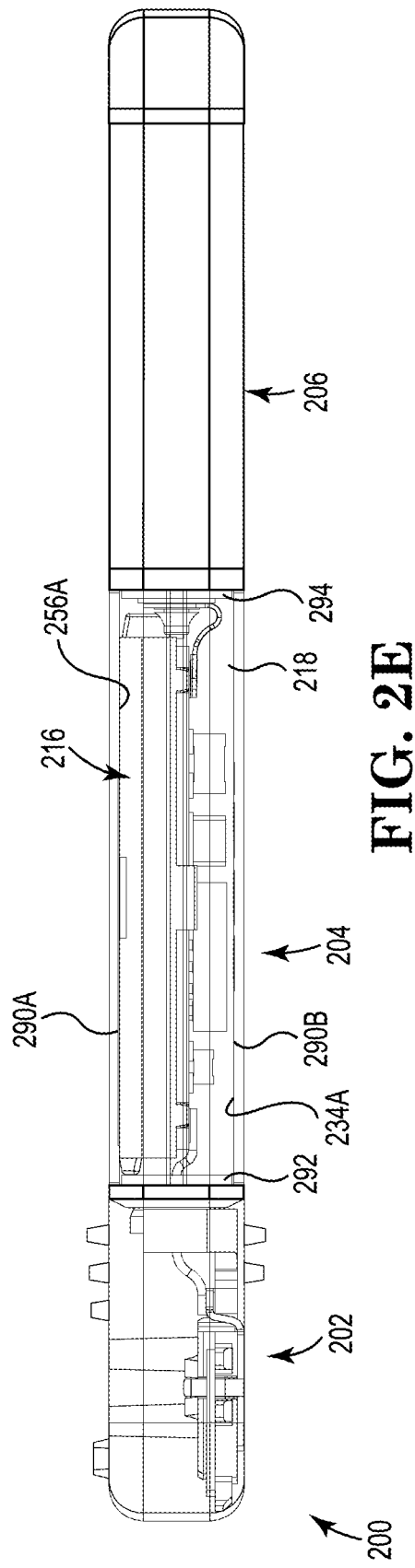

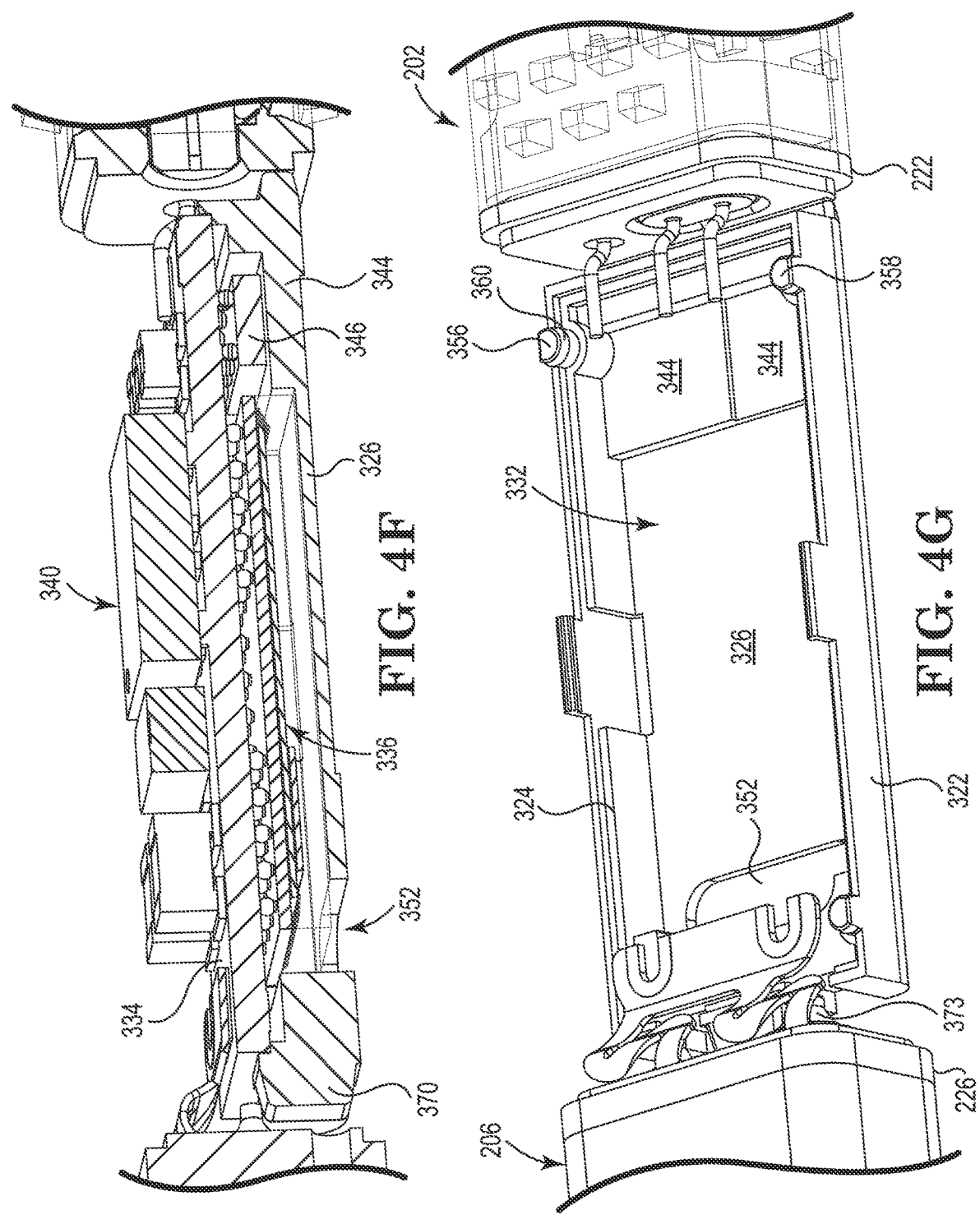

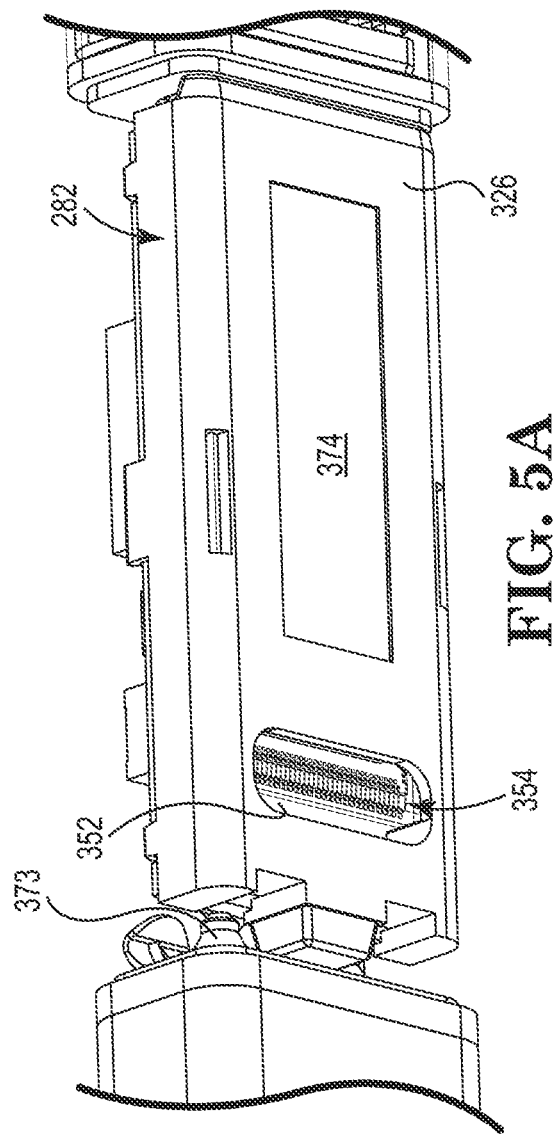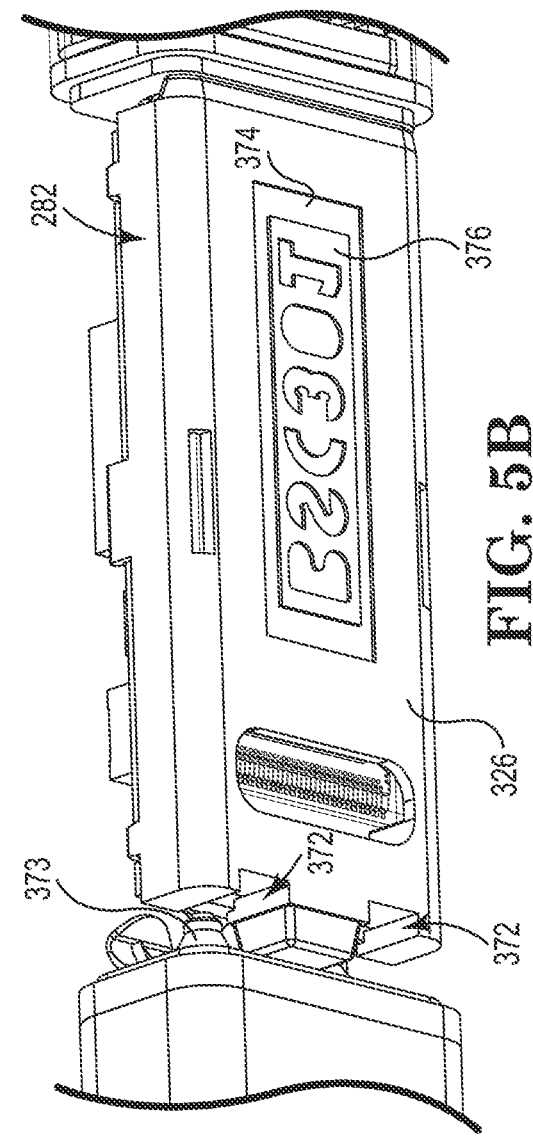

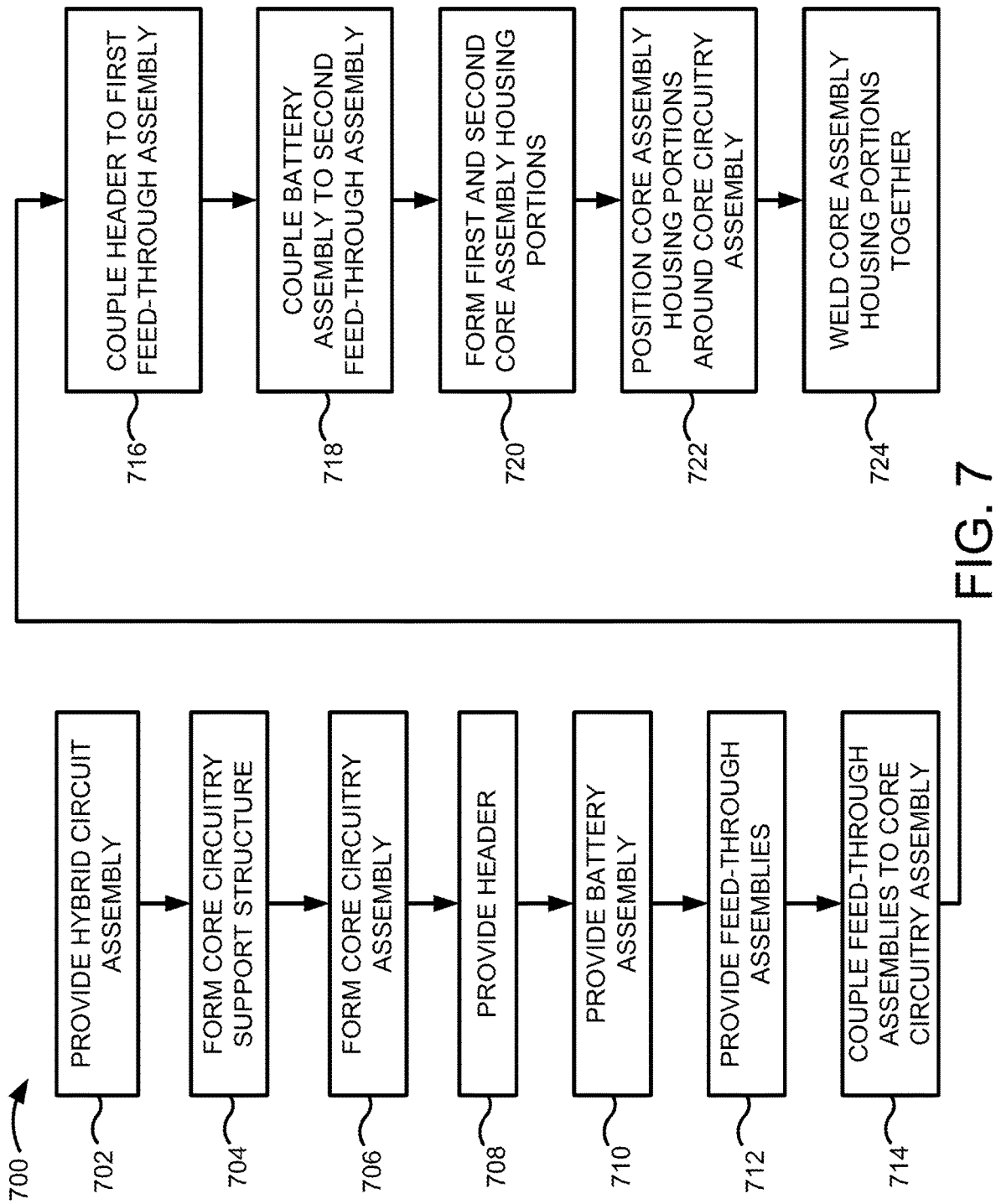

IMD HAVING A CORE CIRCUITRY SUPPORT STRUCTURE

CROSS-REFERENCE TO RELATED APPLICATIONS

This application is a Continuation Application which claims priority to U.S. patent application Ser. No. 17/132,296, filed Dec. 23, 2020, which is a Continuation Application which claims priority to U.S. patent application Ser. No. 16/746,706, filed Jan. 17, 2020, now U.S. Pat. No. 10,881,016, which is a Continuation Application which claims priority to U.S. patent application Ser. No. 16/356,858, filed Mar. 18, 2019, now U.S. Pat. No. 10,542,633, issued Jan. 21, 2020, which is a Continuation Application which claims priority to U.S. patent application Ser. No. 15/489,603 filed Apr. 17, 2017, now issued U.S. Pat. No. 10,542,633, which claims priority to Provisional Application 62/324,202, filed Apr. 18, 2016, which is herein incorporated by reference in its entirety.

TECHNICAL FIELD

Embodiments of the present disclosure relate to medical devices and systems for sensing physiological parameters and/or delivering therapy. More specifically, embodiments of the disclosure relate to design of control circuitry support structures of implantable medical devices.

BACKGROUND

Implantable medical devices (IMDs) may be configured to sense physiological parameters and/or provide therapy and may include one or more electrodes for performing aspects of these functions. Construction of IMDs often involves challenges regarding locating circuitry so that interconnections can be made in a repeatable manner, positional locations are maintained, and ease of manufacturing is increased.

SUMMARY

Embodiments of the disclosure include an implantable medical device having a core circuitry support structure that facilitates locating the core circuitry in space to improve repeatability of interconnections, reliability of spatial location, and ease of manufacture.

In an Example 1, a medical device comprising: a hybrid circuitry assembly; and a core circuitry support structure, comprising: a frame defining a cavity configured to receive at least a portion of the hybrid circuitry assembly, wherein an outer surface of the frame is shaped to correspond to an inside surface of a core assembly housing configured to enclose the hybrid circuitry assembly and the core circuitry support structure.

In an Example 2, the medical device of Example 1, the hybrid circuitry assembly comprises a printed circuit board (PCB) having a first surface and a second, parallel surface.

In an Example 3, the medical device of either of Examples 1 or 2, the frame comprising: a first end wall; a second, opposite end wall; and a pair of parallel, opposed side walls, wherein the first end wall, second end wall, and side walls define the cavity.

In an Example 4, the medical device of any of Examples 1-3, the frame comprising at least one alignment feature, the at least one alignment feature configured to facilitate alignment of the hybrid circuitry assembly with the core circuitry support structure.

In an Example 5, the medical device of Example 4, the PCB comprising at least one alignment notch, wherein the at least one alignment notch is configured to receive the at least one alignment feature.

In an Example 6, the medical device of either of Examples 4 or 5, the at least one alignment feature comprising: a first alignment feature having a first shape a first size; and a second alignment feature having a second shape and a second size, wherein: the second shape is different than the first shape, and/or the second size is different than the first size.

In an Example 7, the medical device of any of Examples 2-6, the core circuitry support structure comprising a shelf extending at least partially around a perimeter of the core circuitry support structure, wherein the shelf is configured to engage a peripheral edge of the first surface of the PCB.

In an Example 8, the medical device of any of Examples 2-7, the hybrid circuitry assembly further comprising: a first set of additional circuitry components coupled to the first side of the PCB; and a second set of additional circuitry components coupled to the second side of the PCB.

In an Example 9, the medical device of any of Examples 3-8, wherein the core circuitry support structure comprises a panel coupled to the first end wall, second end wall and side walls, wherein the first end wall, second end wall, and side walls define the cavity.

In an Example 10, the medical device of either of Examples 8 or 9, further comprising a cover configured to be disposed over the second set of additional circuitry components, the cover comprising an outer surface shaped to correspond to the inner surface of the core assembly housing.

In an Example 11, the medical device of either of Examples 9 or 10, the panel comprising a recess defined in an outside surface of the panel, the recess configured to receive an X-ray identification tag.

In an Example 12, a medical device comprising: a header having a first end and a second end; a feed-through assembly coupled to the second end of the header; and a core assembly coupled, at a first end, to the feed-through assembly, the core assembly comprising: a core assembly housing enclosing an interior space; a core circuitry assembly disposed in the interior space, the core circuitry assembly comprising: a hybrid circuitry assembly; and a core circuitry support structure, the core circuitry support structure comprising a frame defining a cavity that is configured to receive at least a portion of the hybrid circuitry assembly.

In an Example 13, the medical device of Example 12, the hybrid circuitry assembly comprising a printed circuit board (PCB) having a first surface and a second, parallel surface, wherein the core circuitry support structure includes at least one alignment feature, the at least one alignment feature configured to facilitate alignment of the hybrid circuitry assembly with the core circuitry support structure.

In an Example 14, the medical device of Example 13, the PCB comprising at least one alignment notch, wherein the at least one alignment notch is configured to receive the at least one alignment feature.

In an Example 15, a method of manufacturing a medical device, comprising: providing a hybrid circuitry assembly; forming a core circuitry support structure, the core circuitry support structure comprising at least one of an alignment feature configured to facilitate alignment of the hybrid circuitry assembly with the core circuitry support structure and a retaining clip configured to engage at least a portion of the hybrid circuitry assembly; coupling the hybrid circuitry assembly to the core circuitry support structure to form a core circuitry assembly; positioning a first portion and a second portion of a core assembly housing around the core circuitry assembly; and welding the first and second portions together.

In an Example 16, a medical device comprising: a hybrid circuitry assembly comprising a printed circuit board (PCB) having a first surface and a second, parallel surface; and a core circuitry support structure, comprising: a frame defining a cavity configured to receive at least a portion of the hybrid circuitry assembly, wherein an outer surface of the frame is shaped to correspond to an inside surface of a core assembly housing configured to enclose the hybrid circuitry assembly and the core circuitry support structure.

In an Example 17, the medical device of Example 16, the frame comprising: a first end wall; a second, opposite end wall; and a pair of parallel, opposed side walls, wherein the first end wall, second end wall, and side walls define the cavity.

In an Example 18, the medical device of Example 17, the frame comprising at least one alignment feature, the at least one alignment feature configured to facilitate alignment of the hybrid circuitry assembly with the core circuitry support structure.

In an Example 19, the medical device of Example 18, the PCB comprising at least one alignment notch, wherein the at least one alignment notch is configured to receive the at least one alignment feature.

In an Example 20, the medical device of Example 19, the at least one alignment feature comprising: a first alignment feature having a first shape a first size; and a second alignment feature having a second shape and a second size, wherein: the second shape is different than the first shape, and/or the second size is different than the first size.

In an Example 21, the medical device of Example 16, the core circuitry support structure comprising a shelf extending at least partially around a perimeter of the core circuitry support structure, wherein the shelf is configured to engage a peripheral edge of the first surface of the PCB.

In an Example 22, the medical device of Example 17, the hybrid circuitry assembly further comprising: a first set of additional circuitry components coupled to the first side of the PCB; and a second set of additional circuitry components coupled to the second side of the PCB.

In an Example 23, the medical device of Example 22, wherein the core circuitry support structure comprises a panel coupled to the first end wall, second end wall and side walls, wherein the first end wall, second end wall, and side walls define the cavity.

In an Example 24, the medical device of Example 22, further comprising a cover configured to be disposed over the second set of additional circuitry components, the cover comprising an outer surface shaped to correspond to the inner surface of the core assembly housing.

In an Example 25, the medical device of Example 17, the panel comprising a recess defined in an outside surface of the panel, the recess configured to receive an X-ray identification tag.

In an Example 26, a medical device comprising: a header having a first end and a second end; a feed-through assembly coupled to the second end of the header; and a core assembly coupled, at a first end, to the feed-through assembly, the core assembly comprising: a core assembly housing enclosing an interior space; a core circuitry assembly disposed in the interior space, the core circuitry assembly comprising: a hybrid circuitry assembly; and a core circuitry support structure, the core circuitry support structure comprising a frame defining a cavity that is configured to receive at least a portion of the hybrid circuitry assembly.

In an Example 27, the medical device of Example 26, the hybrid circuitry assembly comprising a printed circuit board (PCB) having a first surface and a second, parallel surface, wherein the core circuitry support structure includes at least one alignment feature, the at least one alignment feature configured to facilitate alignment of the hybrid circuitry assembly with the core circuitry support structure.

In an Example 28, the medical device of Example 27, the PCB comprising at least one alignment notch, wherein the at least one alignment notch is configured to receive the at least one alignment feature.

In an Example 29, the medical device of Example 27, the at least one alignment feature comprising: a first alignment feature having a first shape a first size; and a second alignment feature having a second shape and a second size, wherein: the second shape is different than the first shape, and/or the second size is different than the first size.

In an Example 30, the medical device of Example 27, the core circuitry support structure comprising a shelf extending at least partially around a perimeter of the core circuitry support structure, wherein the shelf is configured to engage a peripheral edge of the first surface of the PCB.

In an Example 31, the medical device of Example 27, the hybrid circuitry assembly further comprising: a first set of additional circuitry components coupled to the first side of the PCB; and a second set of additional circuitry components coupled to the second side of the PCB.

In an Example 32, the medical device of Example 31, the frame comprising: a first end wall; a second, opposite end wall; and a pair of parallel, opposed side walls, wherein the first end wall, second end wall, and side walls define the cavity.

In an Example 33, the medical device of Example 31, further comprising a cover configured to be disposed over the second set of additional circuitry components, the cover comprising an outer surface shaped to correspond to the inner surface of the core assembly housing.

In an Example 34, the medical device of Example 32, the panel comprising a recess defined in an outside surface of the panel, the recess configured to receive an X-ray identification tag.

In an Example 35, a method of manufacturing a medical device, comprising: providing a hybrid circuitry assembly; forming a core circuitry support structure, the core circuitry support structure comprising an alignment feature configured to facilitate alignment of the hybrid circuitry assembly with the core circuitry support structure; coupling the hybrid circuitry assembly to the core circuitry support structure to form a core circuitry assembly; positioning a first portion and a second portion of a core assembly housing around the core circuitry assembly; and welding the first and second portions together.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 2D is a side view of the IMD depicted in FIGS. 2A-2C, with the core assembly housing removed, in accordance with embodiments of the disclosure.

FIG. 2E is a side view of the IMD depicted in FIGS. 2A-2D, with the core assembly housing shown as transparent, in accordance with embodiments of the disclosure.

FIGS. 4E and 4F are cross-sectional perspective views of the IMD depicted in FIGS. 2A-2E, with the core assembly housing removed, in accordance with embodiments of the disclosure.

FIG. 4G is a close-up perspective view of the IMD depicted in FIGS. 2A-2E, with the core assembly housing and hybrid circuitry assembly removed, in accordance with embodiments of the disclosure.

FIGS. 5A and 5B are perspective views of a core circuitry assembly, showing application of an X-ray identification tag, in accordance with embodiments of the disclosure.

FIG. 7 is a flowchart depicting an illustrative method of assembling an IMD, in accordance with embodiments of the disclosure.

Figure 1:
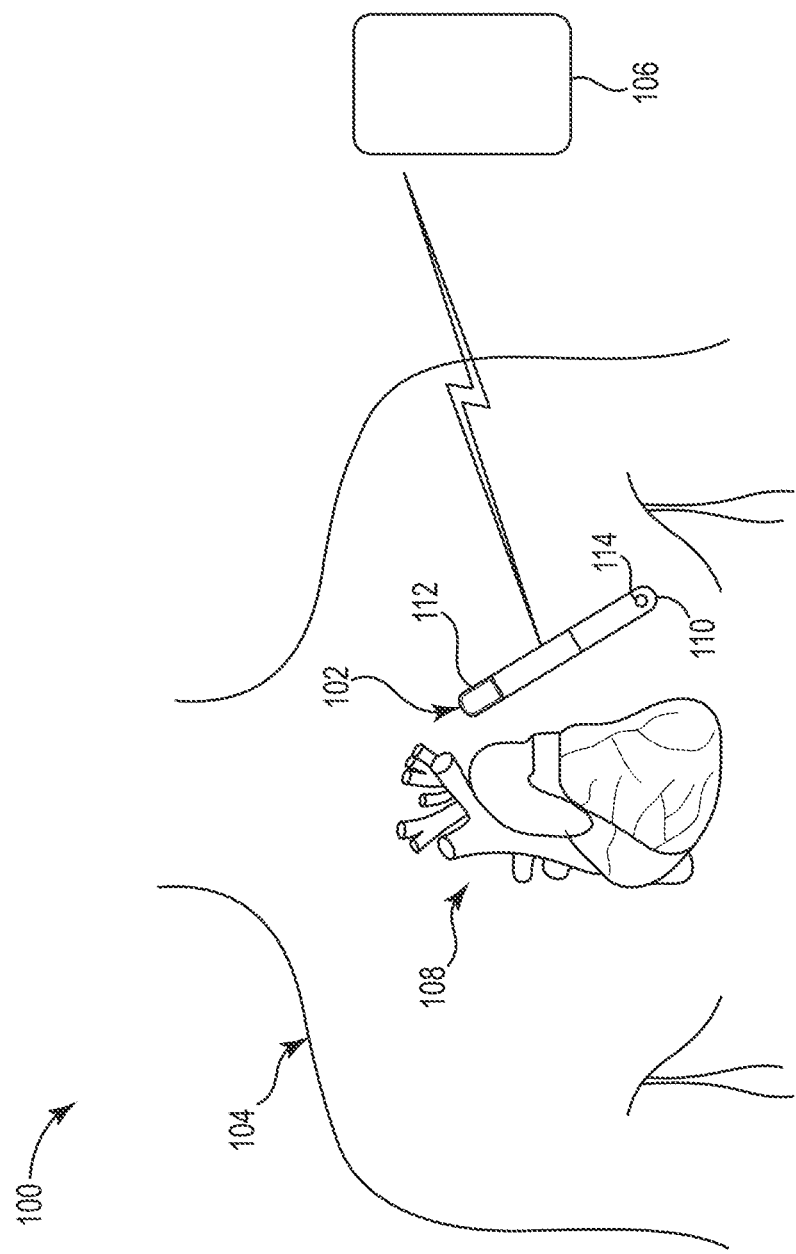
FIG. 1 is a schematic illustration depicting a patient monitoring system, in accordance with embodiments of the disclosure.

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic illustration of a system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like. In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations.

For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient. In embodiments, however, the IMD 102 may include any type of IMD, any number of different components of an implantable system, and/or the like having a housing and being configured to be implanted in a patient's body 104. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the patient's body and/or the IMD 102. In various embodiments, the IMD 102 may include both defibrillation and pacing/CRT capabilities (e.g., a CRT-D device).

As shown, the IMD 102 may include a housing 110 having two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In various embodiments, the IMD 102 may be a pacemaker, an implantable cardioverter defibrillator (ICD) device, or a cardiac resynchronization therapy (CRT) device. In various embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2A:
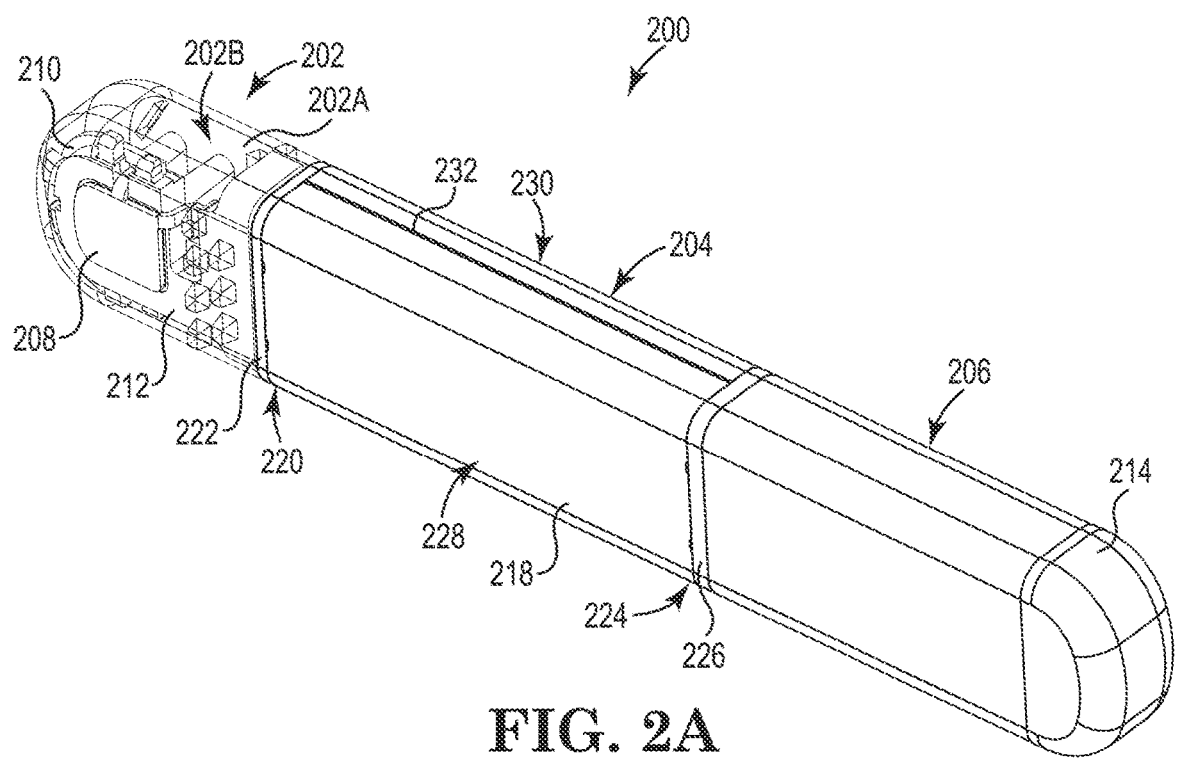
FIG. 2A is a perspective view of an implantable medical device (IMD), in accordance with embodiments of the disclosure.

FIG. 2A is a perspective view of an implantable medical device (IMD) 200, in accordance with embodiments of the disclosure. The IMD 200 may be, or may be similar to, the IMD 102 depicted in FIG. 1. As shown, the IMD 200 may include a header 202 arranged at or near a first end 220 of a core assembly 204. A battery assembly 206 (which may include one or more batteries) is arranged near a second end 224 of the core assembly 204. The header 202 includes a housing 202A that encloses an interior region 202B. The header 202 may house various circuitry components within its interior. The housing 202A may contact a patient's bodily tissue when the IMD 200 is subcutaneously implanted in an implantation location or pocket in the patient's chest or abdomen. The interior region 202B of the header 202 may house circuit components (e.g., an electrode 208 and an antenna 210) positioned and supported by a scaffold assembly 212. As shown, the IMD 200 may include, in addition to the electrode 208, an electrode 214 disposed at an end of the battery assembly 206. In embodiments, the electrode 214 may be integrated with the battery assembly 206, a housing of the battery assembly 206, and/or the like. In order to enable sensing of physiological parameters within the patient, the electrode 208 may be positioned to be flush with an interior surface of the housing 202A of the header 202. In other instances, the electrode 208 may be positioned by the scaffold assembly 212 to form a portion of an exterior surface of the housing 202A of the header 202.

Figure 2B:
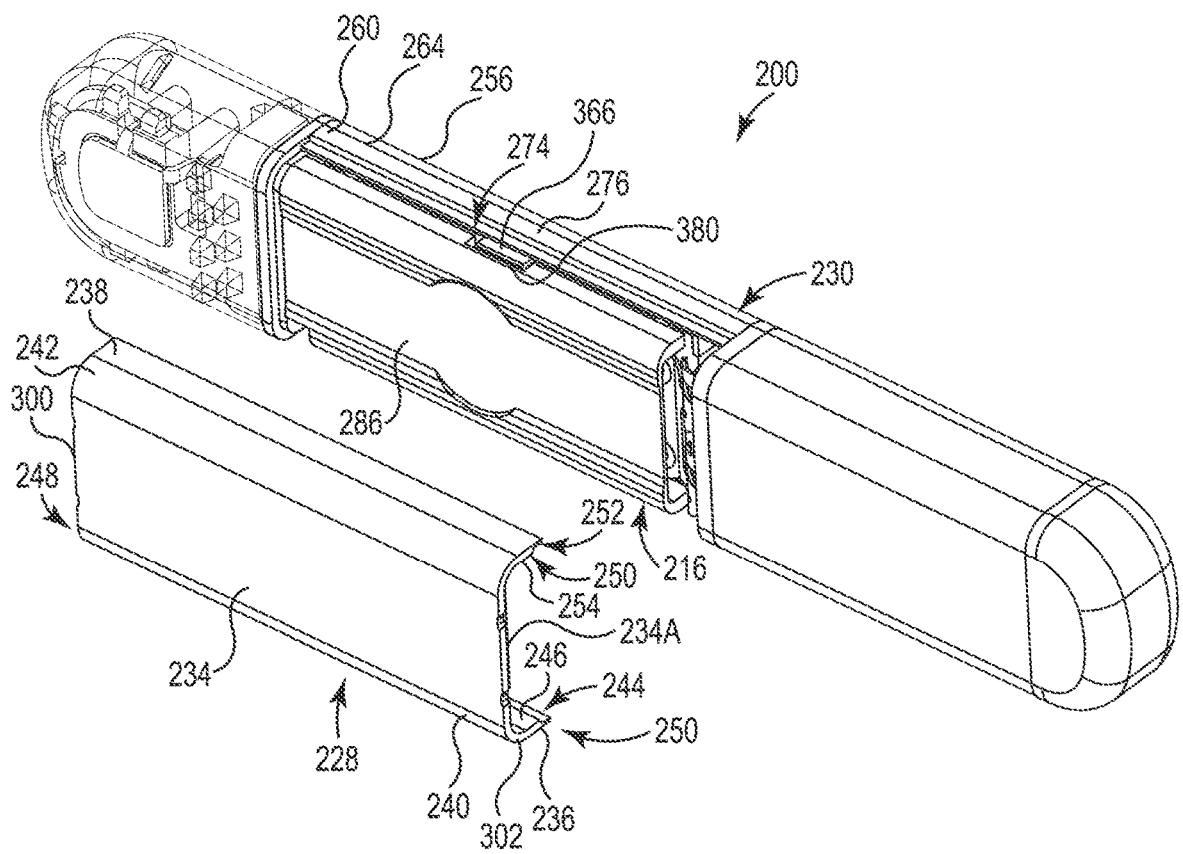
FIGS. 2B and 2C are partially-exploded perspective views of the IMD depicted in FIG. 2A, in accordance with embodiments of the disclosure.

As shown in FIG. 2B, the core assembly 204 includes a core circuitry assembly 216 enclosed within a core assembly housing 218. The core assembly housing 218 is coupled, at the first end 220, to a first feed-through assembly 222, and coupled, at the second end 224, to a second feed-through assembly 226. The feed-through assembly 222 may be configured to provide a throughput for connections configured to connect the circuitry components of the header 202 (e.g., the electrode 208 and the antenna 210) to the core circuitry assembly 216. Similarly, the feed-through assembly 226 may be configured to provide a throughput for connections configured to connect one or more batteries (e.g., which are a part of the battery assembly 206) and/or the electrode 214 to the core circuitry assembly 216.

As illustrated in FIG. 2A, the core assembly housing 204 includes a first portion 228 configured to be coupled to a second portion 230 along a weld seam 232. The first portion 228 and second portion 230 may be coupled together by laser welding, seam welding, and/or the like. In embodiments, a separate weld ring does not need to be used, as a feature of at least one of the first and second portions 228 and 230 acts as a weld ring, protecting the core circuitry assembly 216 from the welding energy (e.g., heat, laser, etc.).

For example, the first portion 228 may include one or more weld joint features configured to be positioned adjacent to one or more corresponding weld joint features on the second portion 230 in preparation for welding. In embodiments, for example, the first portion 228 and the second portion 230 may include a continuous, curved wall (such as, for example, in an implementation of a pacemaker or other implantable pulse generator), a curved wall and a straight wall, a number of curved walls, a number of straight walls, and/or any number of different combinations of these. Each wall of the first portion 228 that is configured to be coupled to a corresponding wall of the second portion 230 may include at least one weld joint feature configured to be positioned adjacent to at least one corresponding feature on the second portion 230, and, in embodiments, vice-versa.

Each weld joint feature includes a thinned leading edge (the edge that is configured to be coupled to the corresponding edge of the other portion of the housing) of a wall. That is, the edge of the wall is thinner than other sections of the wall. In this manner, an edge of one of the two portions can pass over the corresponding edge of the other portion when the two portions are positioned around the core circuitry assembly in preparation for welding. In this manner, the volume enclosed within the housing may be maximized, and the lower edge (i.e., the edge closer to the core circuitry assembly) acts as a weld ring, protecting the core circuitry assembly from the applied energy (e.g., heat, laser, etc.) during a welding procedure. In embodiments, the weld joint feature may include a coined edge of a wall, a flange, and/or the like.

Figure 2C:
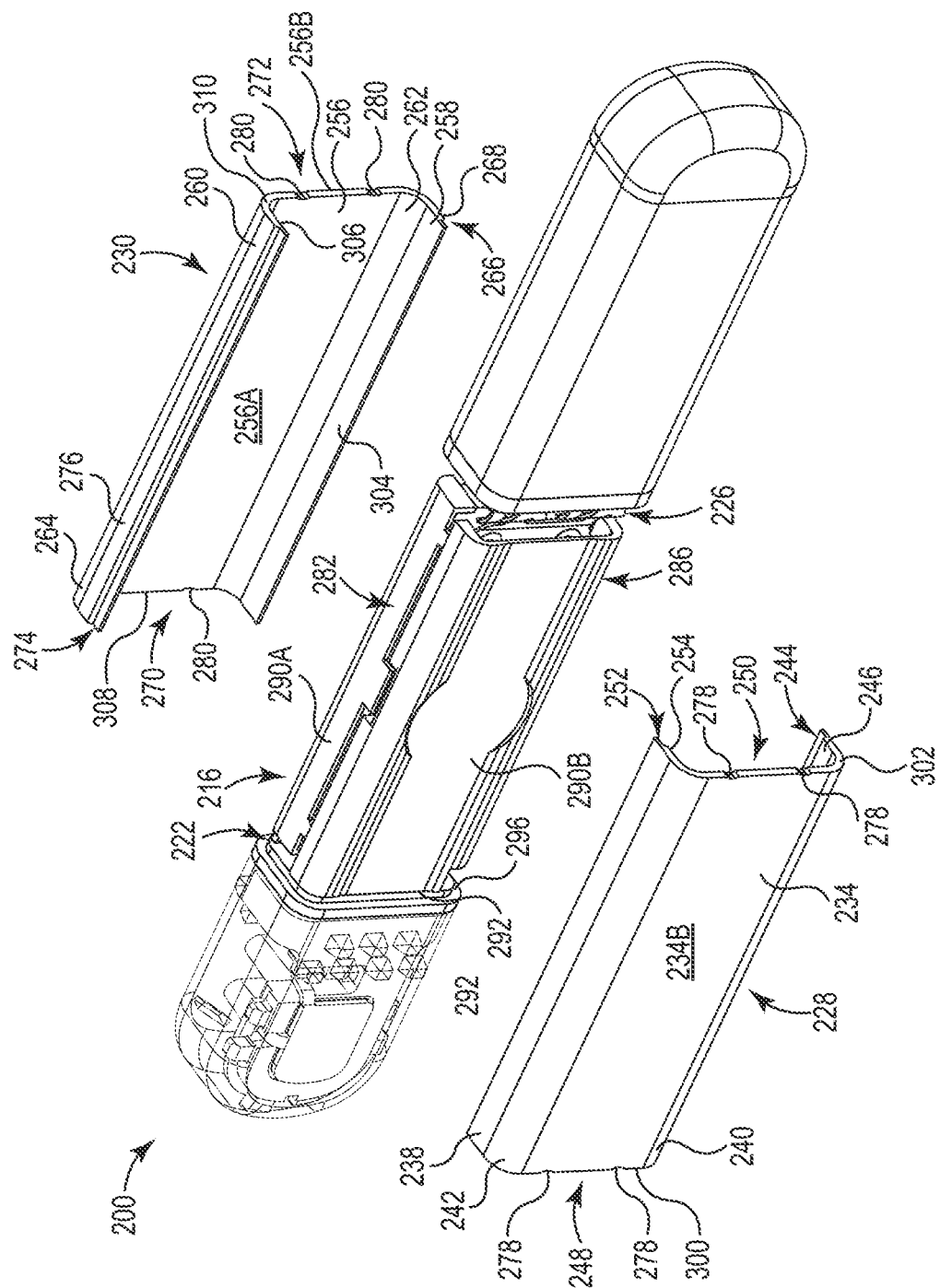

As shown, for example, in FIGS. 2B and 2C, the first portion 228 of the core assembly housing 218 includes a side wall 234, a lower wall 236, and an upper wall 238. The lower wall 236 and the upper wall 238 each extend, perpendicularly (or at least approximately perpendicularly) in a direction away from an inside surface 234A of the side wall 234. As shown, the lower wall 236 is coupled to the side wall 234 by a curved corner portion 240, and the upper wall 238 is coupled to the side wall 234 by a curved corner portion 242. In embodiments, the curved corner portions 240 and 242 may be integrated with the lower and upper walls 236 and 238, respectively, the side wall 234, and/or the like. That is, for example, the first portion 228 may be a single piece of metal, formed in a press or a mold. In embodiments, the curved corner portions 240 and 242 may be separate components. The curved corner portions 240 and 242 each may be designed to have any desirable radius of curvature. For example, the curved corner portions 240 and 242 each may be configured to have a radius of curvature that provides a desired amount of volume enclosed within the core assembly housing 218.

As illustrated, for example, in FIGS. 2B and 2C, the lower wall 236 includes a flange 244 that is recessed with respect to an inside surface 246 of the lower wall 236, and that extends from a first end 248 of the first portion 228 to a second end 250 thereof. The flange 244 may be a thinned portion of the lower wall 236. In embodiments, the flange 244 may be welded to the lower wall 236. Similarly, the upper wall 238 includes a flange 252 that is recessed with respect to an inside surface 254 of the upper wall 238, and that extends from the first end 248 of the first portion 228 to the second end 250 thereof. The flange 252 may be a thinned portion of the upper wall 238. In embodiments, the flange 252 may be welded to the upper wall 238.

As is also shown, for example, in FIGS. 2B and 2C, the second portion 230 of the core assembly housing 218 includes a side wall 256, a lower wall 258, and an upper wall 260. The lower wall 258 and the upper wall 260 each extend, perpendicularly (or at least approximately perpendicularly) in a direction away from an inside surface 256A of the side wall 256. As shown, the lower wall 258 is coupled to the side wall 256 by a curved corner portion 262, and the upper wall 260 is coupled to the side wall 256 by a curved corner portion 264. In embodiments, the curved corner portions 262 and 264 may be integrated with the lower and upper walls 258 and 260, respectively, the side wall 256, and/or the like. That is, for example, the second portion 230 may be a single piece of metal, formed in a press or a mold. In embodiments, the curved corner portions 262 and 264 may be separate components. The curved corner portions 262 and 264 each may be designed to have any desirable radius of curvature such as, for example, a radius of curvature that is identical or similar to the radius of curvature of each of the curved corner portions 240 and 242. For example, the curved corner portions 262 and 264 each may be configured to have a radius of curvature that provides a desired amount of volume enclosed within the core assembly housing 218.

As illustrated, for example, in FIGS. 2B and 2C, the lower wall 258 includes a flange 266 that is recessed with respect to an outside surface 268 of the lower wall 258, and that extends from a first end 270 of the second portion 230 to a second end 272 thereof. The flange 266 may be a thinned portion of the lower wall 258. In embodiments, the flange 266 may be welded to the lower wall 258. Similarly, the upper wall 260 includes a flange 274 that is recessed with respect to an outside surface 276 of the upper wall 260, and that extends from the first end 270 of the second portion 230 to the second end 272 thereof. The flange 274 may be a thinned portion of the upper wall 260. In embodiments, the flange 274 may be welded to the upper wall 260. The core assembly housing 218 may also include notches 278 defined in the first and second ends 248 and 250, respectively, of the first portion 228, and extending from the inside surface 234A to the outside surface 234B of the side wall 234. Similarly, the core assembly housing 218 may also include notches 280 defined in the first and second ends 270 and 272, respectively, of the second portion 230, and extending from the inside surface 256A to the outside surface 256B of the side wall 256. When the first portion 228 is brought together with the second portion 230, the flange 244 is positioned adjacent to the flange 266, and the flange 252 is positioned adjacent to the flange 274. The portions 228 and 230 are welded together along the flanges 244, 266 and 252, 274 to enclose the core circuitry assembly 216.

As shown in FIGS. 2B-2E, the core circuitry assembly 216 includes a core circuitry support structure 282 disposed within the core assembly housing 218. A hybrid circuit assembly 284, which includes the core circuitry such as, for example, a printed circuit board (PCB) and other circuitry components, is coupled, on a first side (not shown in FIGS. 2B-2E) of the hybrid circuit assembly 284 to the core circuitry support structure 282. A cover 286 is disposed over a second side 288 of the hybrid circuit assembly 284. The cover 286 may be configured according to any number of different shapes, including, for example, a shape that corresponds to the shape of the inside surfaces 234A, 246, and 254 of the first portion 234 of the core assembly housing 218. In embodiments in which the core circuitry support structure 282 includes retaining clips 366, the cover 286 may include notches 380 corresponding to, and allowing room for, retaining clips 366 disposed on the core circuitry support structure 282. In embodiments, the cover 286 may include any number of other features configured to correspond to any number of other features of the core circuitry support structure 282, the core assembly housing 218, and/or other component of the IMD 200.

The core circuitry assembly 216 may be configured to enhance the available space within the core assembly. In embodiments, as shown, the core circuitry support structure 282 may include an outside surface 290A and the cover 286 may include an outside surface 290B. The outside surfaces 290A and 290B may be configured to align in at least approximately a same plane (or set of planes or curved surfaces) as a first interface surface 292 defined on the first feed-through assembly 222 and a second interface surface 294 defined on the second feed-through assembly 226. The first and second interface surfaces 292 and 294 may extend around a perimeter of each of the first and second feed-through assemblies 222 and 226, respectively, and may extend at least approximately orthogonally away from third and fourth interface surfaces 296 and 298, respectively, which also may extend around a perimeter of each of the first and second feed-through assemblies 222 and 226, respectively.

During assembly, the first and second portions 228 and 230 of the core assembly housing 218 are brought together such that the inside surface 246 of the lower wall 236 of the first portion 228, the inside surface 234A of the side wall 234 of the first portion 228, and the inside surface 254 of the upper wall 238 of the first portion 228 interface with (e.g., are disposed in contact with) corresponding sections of the first and second interface surfaces 292 and 294; and a first edge surface 300 and a second edge surface 302 of the first portion 228 interface with the first and second interface surfaces 296 and 298, respectively. Similarly, during assembly, an inside surface 304 of the lower wall 258 of the second portion 230, the inside surface 256A of the side wall 256 of the second portion 230, and an inside surface 306 of the upper wall 260 of the second portion 230 interface with (e.g., are disposed in contact with) corresponding sections of the first and second interface surfaces 292 and 294; and a first edge surface 308 and a second edge surface 310 of the second portion 230 interface with the first and second interface surfaces 296 and 298, respectively. In this manner, when the core assembly housing 218 is welded together, the inside surfaces of the core assembly housing 218 may interface with the outside surface 290A of the core circuitry support structure 282 and the outside surface 290B of the cover 286. In embodiments, the inside surfaces of the core assembly housing 218 may not actually contact the outside surfaces 290A and 290B of the core circuitry support structure 282 and cover 286, respectively, but may be configured to reduce a gap between the surfaces. According to embodiments, the outside surfaces 290A and 290B of the core circuitry support structure 282 and cover 286, respectively, may be designed to have shapes that correspond to the shapes of the inside surfaces of the core assembly housing 218.

In embodiments, the core circuitry support structure 282 and/or the cover 286 may be configured such that an air gap is formed adjacent to the weld seam 232. The air gap may be provided by designing the core circuitry support structure 282 and/or the cover 286 to have a certain perimeter. In embodiments, the air gap may be provided be designing a channel or thinned portion into the core circuitry support structure 282 and/or the cover 286. The air gap may be less than 0.1 inches wide (as measured between an outside surface of the core circuitry support structure 282 or the cover 286 and an inside surface of the core assembly housing 218. In embodiments, the air gap may be approximately 0.010 inches wide, or any other desired width. In this manner, the air gap may facilitate preventing overheating of the core circuitry support structure 282 and/or the cover 286 during welding of the core circuitry assembly 218 together by reducing contact with the core assembly housing 218 and by providing an insulation of air between the core circuitry support structure 282 and/or the cover 286 and the core assembly housing 218. According to embodiments, aspects of the core circuitry support structure 282 may be designed to facilitate providing gaps of any desired width between the outside surface 290A thereof and any number of different inside surfaces of the core assembly housing 218.

The illustrative IMD 200 shown in FIGS. 2A-2E is not intended to suggest any limitation as to the scope of use or functionality of embodiments of the subject matter disclosed throughout this disclosure. Neither should the illustrative IMD 200 be interpreted as having any dependency or requirement related to any single component, feature, or combination of components or features illustrated in FIGS. 2A-2E. For example, in embodiments, the illustrative IMD 200 may include different and/or additional components and/or features. Any number of other components, features, or combinations of components or features can be integrated with the illustrative IMD 200 depicted in FIGS. 2A-2E, all of which are considered to be within the ambit of this disclosure. Additionally, any one or more of the components and/or features depicted in FIGS. 2A-2E can be, in embodiments, integrated with various ones of the other components and/or features depicted therein (and/or components and/or features not illustrated).

FIGS. 3A-3E depict various views of the core circuitry support structure 282, in accordance with embodiments of the disclosure. FIGS. 4A-4E depict various views of the core circuit assembly 216, and may be referred to below to further clarify the description. As shown, the core circuitry support structure 282 includes a first end 312 configured to be disposed adjacent the first feed-through assembly 222, and a second end 314 configured to be disposed adjacent the second feed-through assembly 226. The core circuitry support structure 282 includes a frame 316 having a first end wall 318 disposed at or near the first end 312 of the core circuitry support structure 282, a second end wall 320 disposed at or near the second end 314 of the core circuitry support structure 282, and two parallel, opposed side walls 322 and 324 extending between the first and second end walls 318 and 320. A panel 326, oriented at least approximately perpendicular to the walls 318, 320, 322, and 324, extends between the first and second end walls 318 and 320, and is coupled to the side walls 322 and 324 via curved corner walls 328 and 330, respectively. In embodiments, the curved corner walls 328 and 330 each may be designed to have any desirable radius of curvature such as, for example, a radius of curvature that is identical or similar to (or otherwise designed to complement/correspond to) the radius of curvature of each of the curved corner portions 262 and 264, respectively, of the second portion 230 of the core housing assembly 218.

The end walls 318 and 320, side walls 322 and 324, corner walls 328 and 330, and panel 326, define a cavity 332 configured to receive at least a portion of the hybrid circuit assembly 284. As shown, for example, in FIGS. 4D-4F, the hybrid circuit assembly 284 may include a PCB 334, a first set 336 of additional circuitry components disposed on a first surface 338 of the PCB 334, and a second set 340 of additional circuitry components disposed on a second, opposite, surface 342 of the PCB 334. The first and second surface 338 and 342 may be at least approximately parallel. As shown, the cavity 332 may include one or more raised floor sections 344 that correspond to another set 346 of circuitry components having a lower profile with respect to the first surface 338 of the PCB 334. In embodiments, the cavity may have a flat floor defined by the panel 326. A raised block 348 having a window notch 350 defined therein may be disposed in the cavity 332 near the second end 314 of the core circuitry support structure 282, corresponding to a portion of the first surface 338 of the PCB 334 having no additional circuitry components (or additional circuitry components having a lower profile with respect to the first surface 338). The window notch 350 may be aligned with a window 352 defined in the panel 326. The window 352 may be configured to expose a communication component 354 of the hybrid circuit assembly 284. The communication component 354 may include an antenna, an inductive coil (e.g., for receiving wireless energy to recharge one or more batteries), and/or the like.

As is further shown in FIGS. 3A-3E, the core circuitry support structure 282 includes a number of alignment features 356 configured to engage, abut, and/or otherwise interface with, corresponding alignment notches 358 defined in the PCB 334. Each alignment feature 356 may include a cap 360 disposed at an end of a post 362 that extends away from a shelf 364. The shelf 364 extends along the periphery of core circuitry support structure 282 and is defined in the end walls 318 and 320 and the side walls 322 and 234. The PCB 334 is configured to be received into the cavity 332 such that a peripheral edge of the first side 338 of the PCB 334 engages the shelf 364. The alignment features 356 are configured to be received in the corresponding alignment notches 358, thereby facilitating efficient and accurate alignment of the hybrid circuit assembly 284 within the core circuitry support structure 282 in a manufacturing setting. In this manner, for example, the hybrid circuit assembly 284 may be configured to fit together with the core circuitry support structure 282 in one orientation, to facilitate ease of manufacture.

Figure 3A:
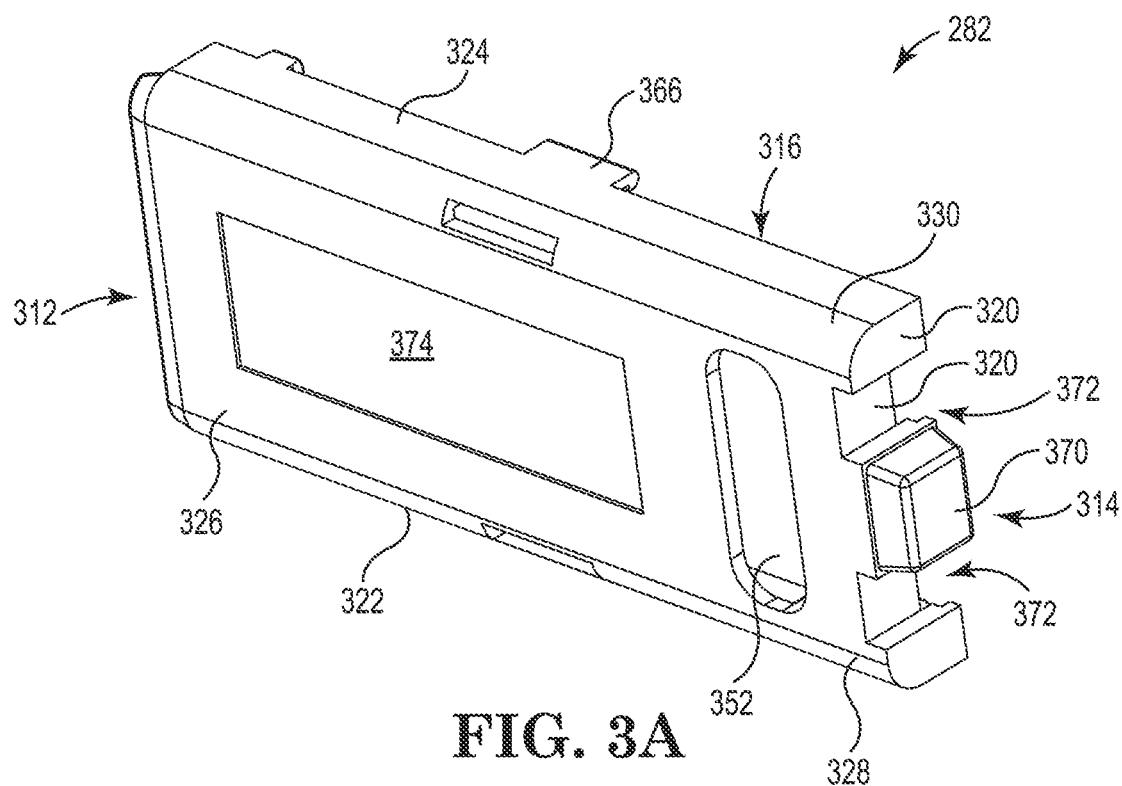
FIG. 3A is a perspective view of a core circuitry support structure, in accordance with embodiments of the disclosure.
Figure 3B:
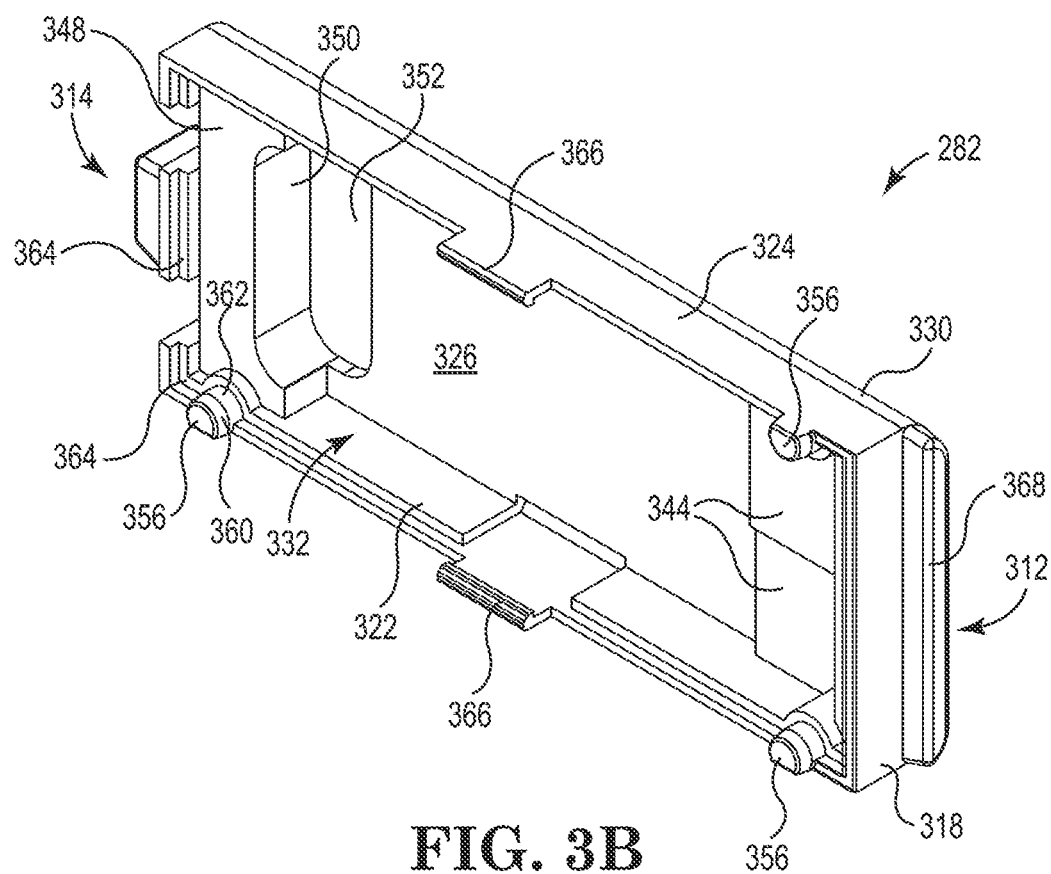
FIG. 3B is another perspective view of the core circuitry support structure depicted in FIG. 3A, in accordance with embodiments of the disclosure.
Figure 3C:
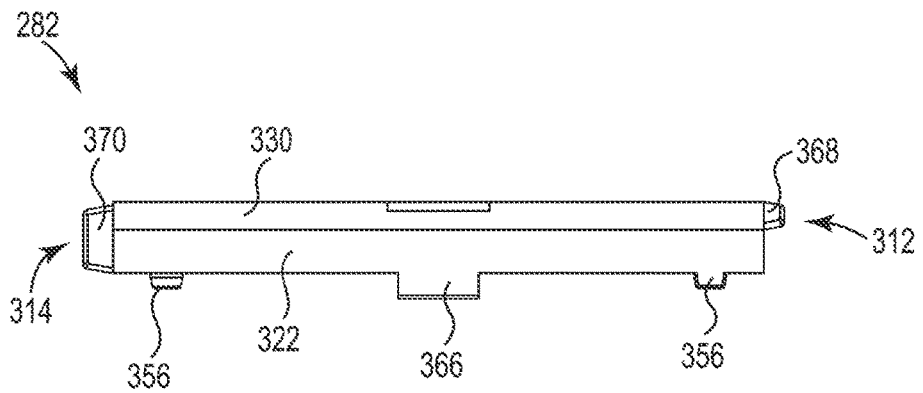
FIG. 3C is a side view of the core circuitry support structure depicted in FIGS. 3A and 3B, in accordance with embodiments of the disclosure.
Figures 3D, 3E:
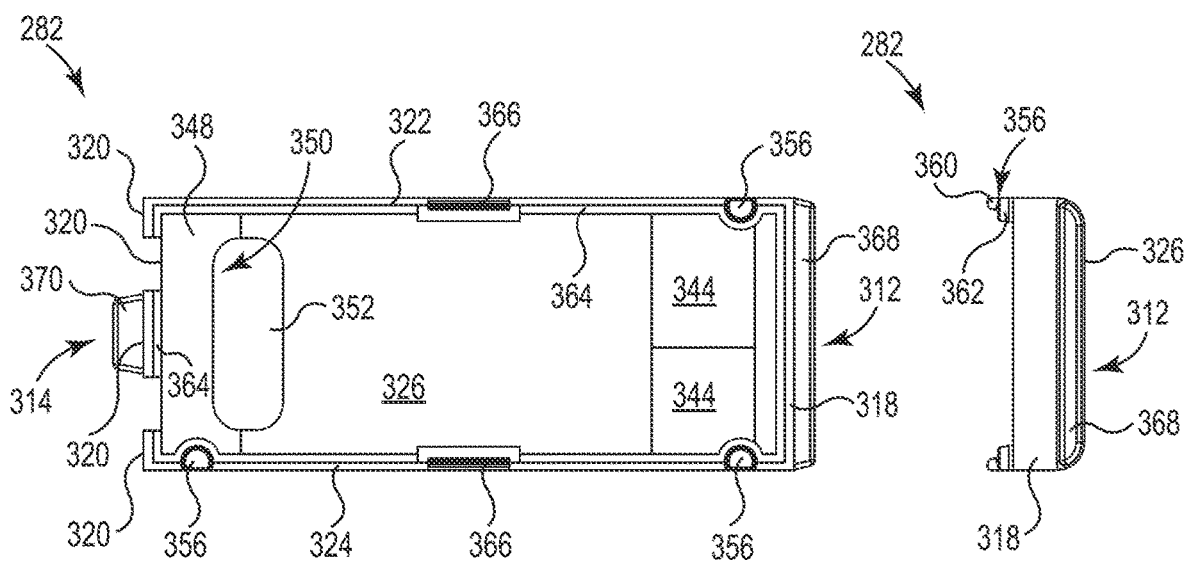
FIG. 3D is a top view of the core circuitry support structure depicted in FIGS. 3A-3C, in accordance with embodiments of the disclosure.
FIG. 3E is a front view of the core circuitry support structure depicted in FIGS. 3A-3D, in accordance with embodiments of the disclosure.
Figure 4A:
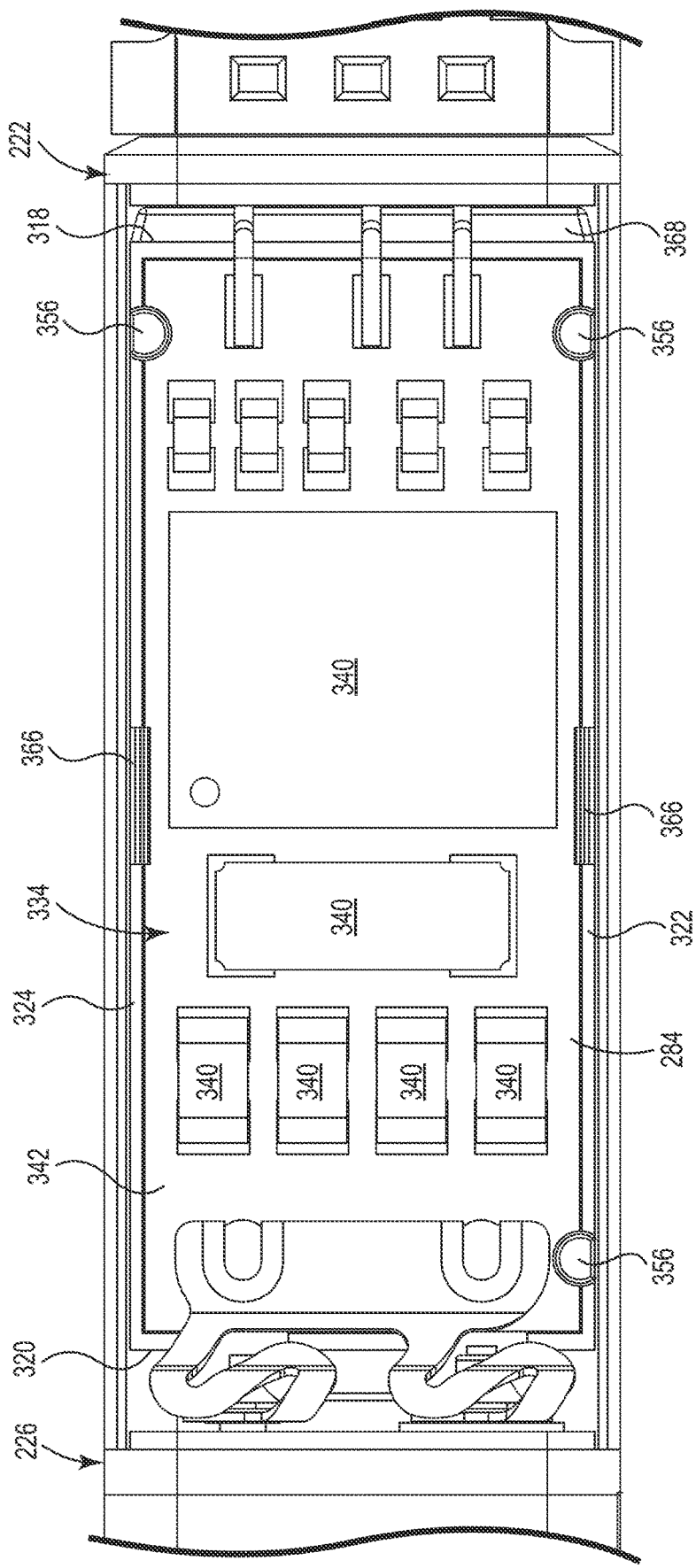
FIG. 4A is a close-up top view of the IMD depicted in FIGS. 2A-2E, with the core assembly housing removed, in accordance with embodiments of the disclosure.
Figure 4B:
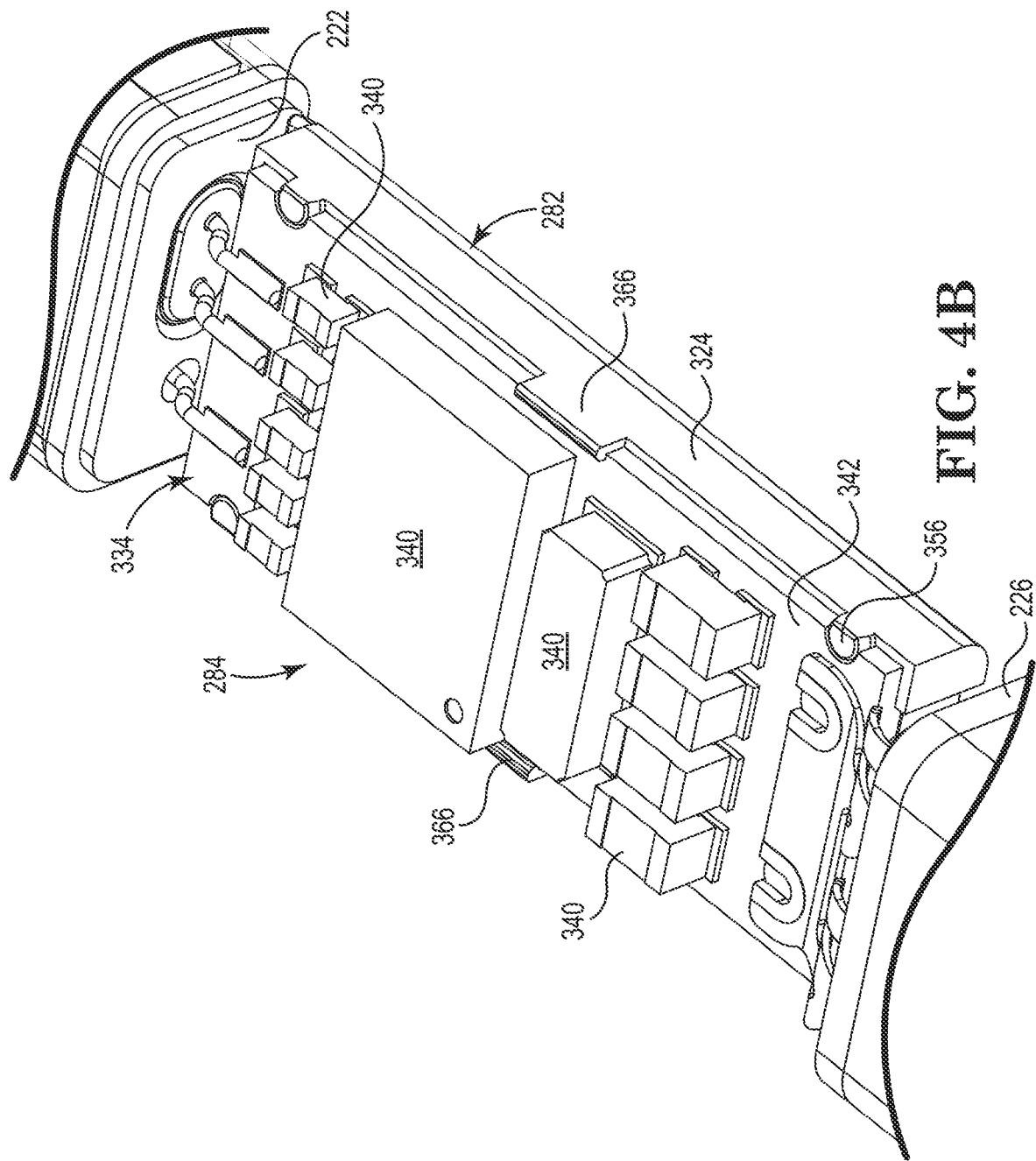
FIG. 4B is a close-up perspective view of the IMD depicted in FIGS. 2A-2E, with the core assembly housing removed, in accordance with embodiments of the disclosure.
Figure 4C:
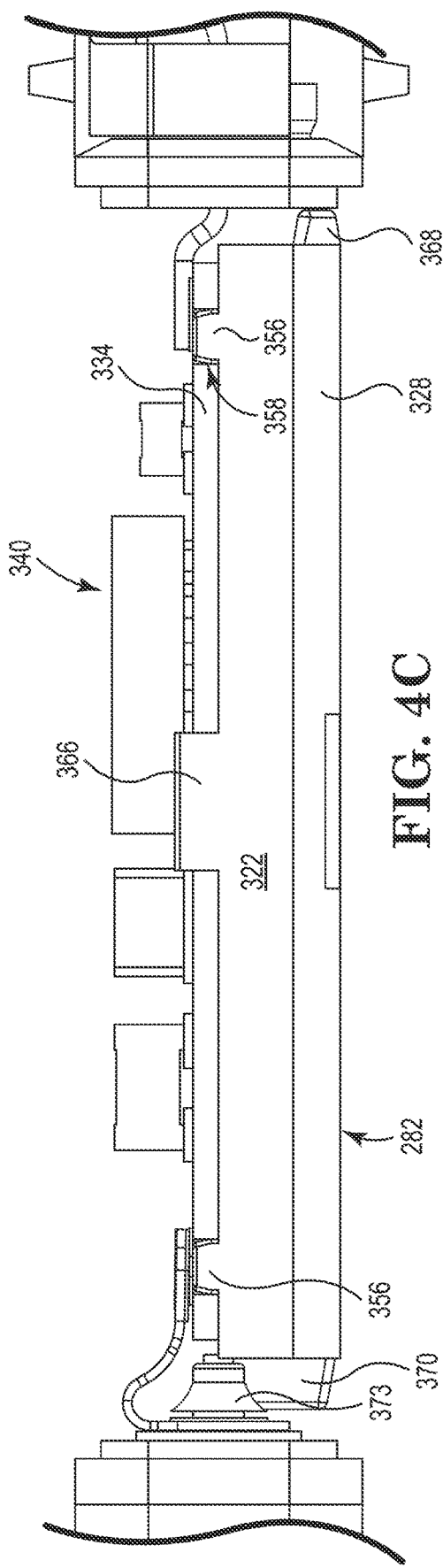
FIG. 4C is a side view of the IMD depicted in FIGS. 2A-2E, with the core assembly housing removed, in accordance with embodiments of the disclosure.
Figure 4D:
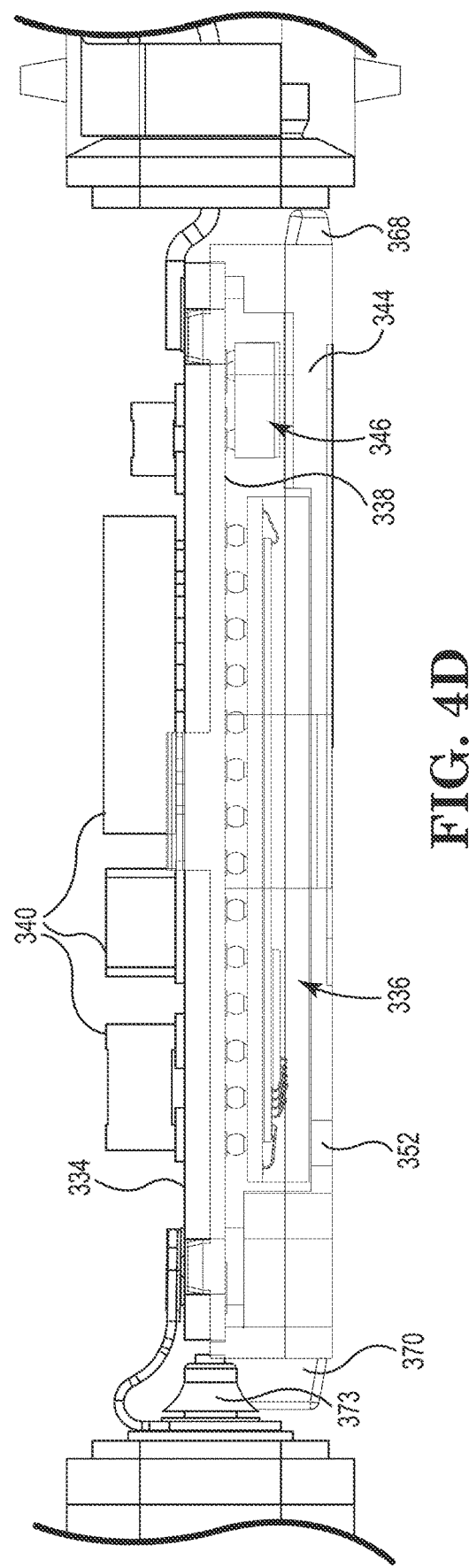
FIG. 4D is a side view of the IMD depicted in FIGS. 2A-2E, with the core assembly housing removed and the core circuitry support structure shown as transparent, in accordance with embodiments of the disclosure.
Figure 4E:
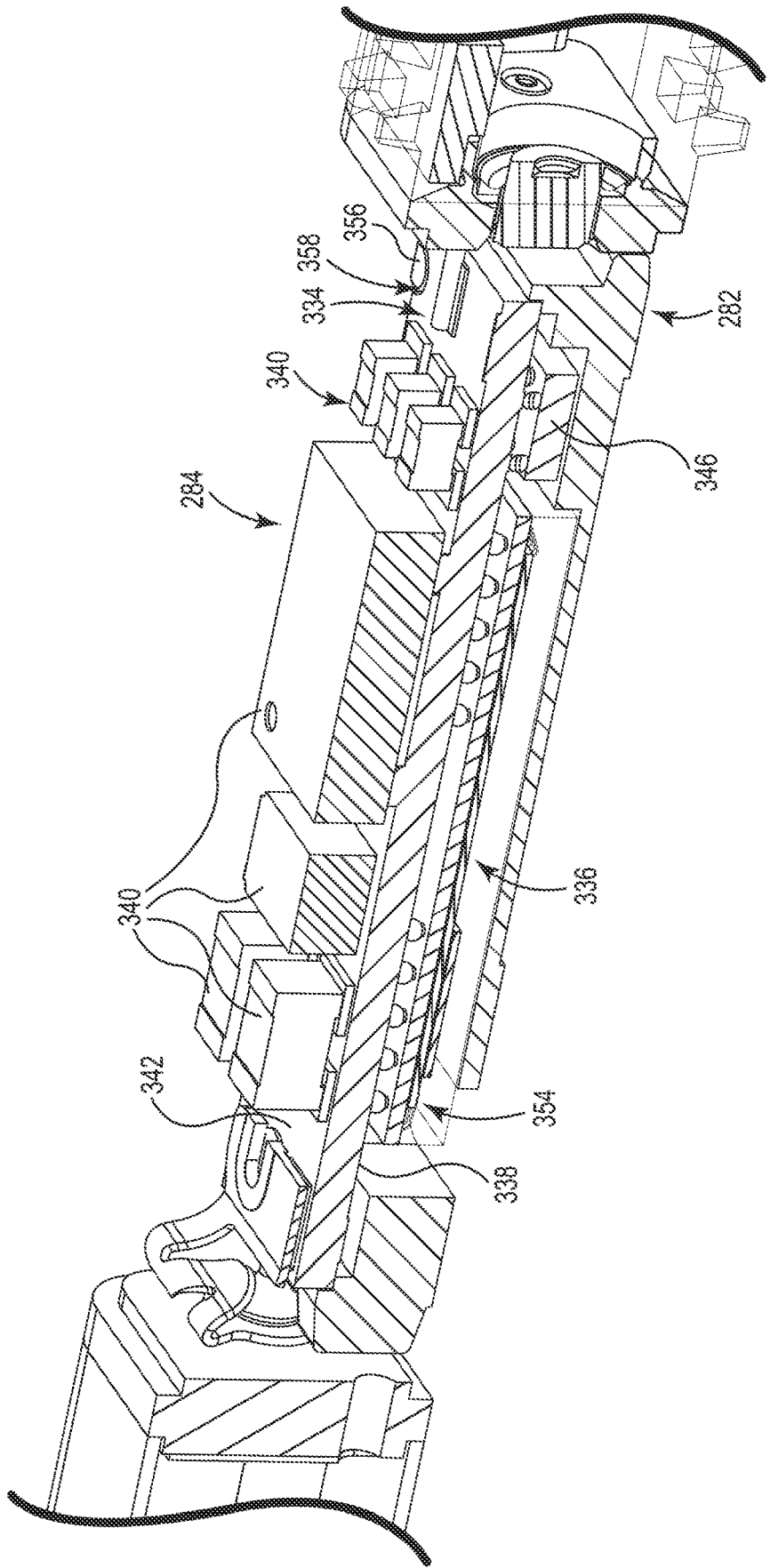

As shown, for example, in FIGS. 3B, 3D, and 3E, the core circuitry support structure 282 may include three alignment features 356. In other embodiments, the core circuitry support structure 282 may include one or two alignment features 356. In embodiments, the core circuitry support structure 282 may include more than three alignment features. According to embodiments, at least one of the alignment features 356 may be of a different size and/or shape than at least one other alignment feature 356. The cap 360 may, in embodiments, include a lip configured to engage a peripheral edge of the second surface 342 of the PCB 334 to facilitate holding the PCB 334 in place. In other embodiments, the cap 360 may be configured to function as a stop. The top of the cap 360 may, in embodiments, be at least approximately flush with the second surface 342 of the PCB 334. The core circuitry support structure 282 also may include one or more retaining clips 366 configured to engage a peripheral edge of the second surface 342 of the PCB 334 to facilitate holding the PCB 334 in place.

As shown, the core circuitry support structure 282 includes a first spacer 368 extending from the first end wall 318 and configured to maintain a space between the first end wall 318 and the first feed-through assembly 222; and a second spacer 370 extending from the second end wall 320 and configured to maintain a space between the second end wall 320 and the second feed-through assembly 226. Notches 372 defined in the second end wall 320 may provide room for feed-through circuitry and/or other components such as, for example, battery terminals 373. As shown in FIG. 3A and FIGS. 5A and 5B, a recess 374 may be defined in the panel 326 and configured to receive an x-ray identification tag 376. The x-ray identification tag 376 may be disposed in the recess 374 using an adhesive, laser welding, etching, and/or the like.

As used herein, the terms "side wall," "lower wall," "upper wall," "upward," and "downward" are used to refer to the specific features to which they refer, but are characterized in the context of the illustrations for clarity and to describe relative orientations of features with respect to other features, and are not intended to imply any particular orientation of the IMD 200, or absolute (or preferred) orientations of features thereof. That is, for example, even if the IMD 200 were to be rotated around a longitudinal axis such that the outer surface 234B of the side wall 234 was parallel to a horizontal plane, the side wall 234 would still be referred to, for the purposes of this disclosure, as a "side wall."

Figure 6A:
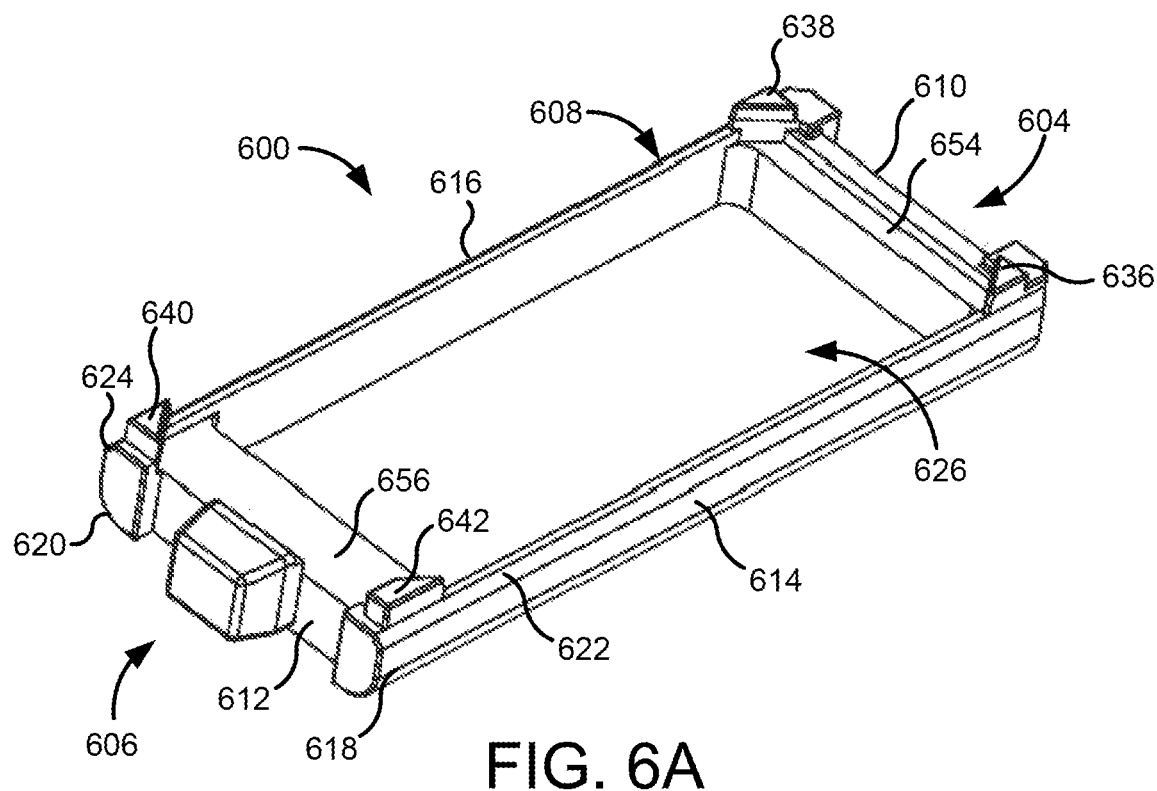
FIGS. 6A and 6B are perspective views of a core circuit support structure, in accordance with embodiments of the disclosure.
Figure 6B:
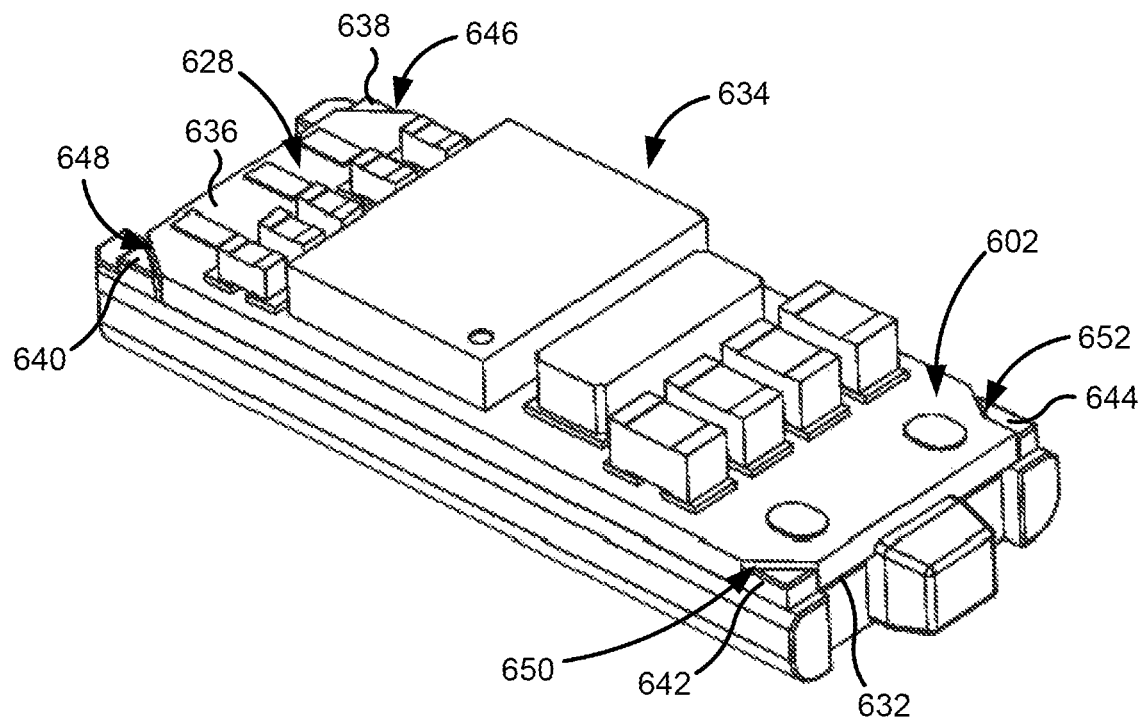

According to embodiments, core circuitry support structures may be designed according to any number of other configurations. FIGS. 6A and 6B depict another core circuitry support structure 600 configured to receive a hybrid circuitry assembly 602 in accordance with embodiments of the disclosed subject matter. The core circuitry support structure 600 may be designed to facilitate injection molding, which may, in embodiments, reduce costs of manufacturing the component.

As shown, the core circuitry support structure 600 includes a first end 604 configured to be disposed adjacent a first feed-through assembly (e.g., the feed-through assembly 222 depicted in FIGS. 2A-2D), and a second end 606 configured to be disposed adjacent a second feed-through assembly (e.g., the feed-through assembly 226 depicted in FIGS. 2A-2D). The core circuitry support structure 600 includes a frame 608 having a first end wall 610 disposed at or near the first end 604 of the core circuitry support structure 600, a second end wall 612 disposed at or near the second end 606 of the core circuitry support structure 600, and two parallel, opposed side walls 614 and 616 extending between the first and second end walls 610 and 612. In embodiments, in contrast with embodiments discussed above with regard, for example, to FIGS. 3A-3E, the frame 608 may not include a panel extending between the walls 610 and 612. In other embodiments, the frame 608 may include a panel, oriented at least approximately perpendicular to the walls 610, 612, 614, and 616, and extending between the first and second end walls 610 and 612. In embodiments, the frame 608 may include curved corner walls 618 and 620, and each may be designed to have any desirable radius of curvature such as, for example, a radius of curvature that is identical or similar to (or otherwise designed to complement/correspond to) the radius of curvature of each of the curved corner portions 262 and 264, respectively, of the second portion 230 of the core housing assembly 218. As shown in FIGS. 6A and 6B, the frame 608 may also include angled upper corner walls 622 and 624.

The end walls 610 and 612, side walls 614 and 616 define a cavity 626 configured to receive at least a portion of the hybrid circuit assembly 602. The hybrid circuit assembly 602 may include a PCB 628, a first set (not shown) of additional circuitry components disposed on a first surface 632 of the PCB 628, and a second set 634 of additional circuitry components disposed on a second, opposite, surface 636 of the PCB 628. The first and second surfaces 632 and 636 may be at least approximately parallel.

As is further shown in FIGS. 6A and 6B, the core circuitry support structure 600 includes a number of alignment features 638, 640, 642, and 644 configured to engage, abut, and/or otherwise interface with, corresponding alignment notches 646, 648, 650, and 652, respectively, defined in the PCB 628. A first shelf portion 654 extends along the inside of the first wall 610 between the first side wall 614 and the second side wall 616. A second shelf portion 656 extends along the inside of the second wall 612 between the first side wall 614 and the second side wall 616. The PCB 628 is configured to be received into the cavity 626 such that a peripheral edge of a portion of the first side 632 of the PCB 628 engages the first shelf portion 654 and a peripheral edge of another portion of the first side 632 of the PCB 628 engages the second shelf portion 656.

The alignment features 638, 640, 642, and 644 are configured to be received in the corresponding alignment notches 646, 648, 650, and 652, thereby facilitating efficient and accurate alignment of the hybrid circuit assembly 602 within the core circuitry support structure 600 in a manufacturing setting. To facilitate this alignment, as shown, at least one alignment feature may have a different size and/or shape than at least one other alignment feature. For example, three of the alignment features 638, 640, and 642 may all have a similar or identical shape, while a fourth alignment feature 644 may have a shape that is different than the shape of the other three alignment features 638, 640, and 642. Similarly, at least one of the corresponding alignment notches may have a different size and/or shape than at least one other alignment notch (e.g., in a manner corresponding to the alignment features). That is, for example, the corresponding alignment notches 646, 648, and 650, may all have a similar or identical shape, while the fourth alignment notch 652 may have a shape that is different than the shape of the other three alignment notches 646, 648, and 650. In this manner, for example, the hybrid circuit assembly 602 may be configured to fit together with the core circuitry support structure 600 in one orientation, to facilitate ease of manufacture.

As shown, for example, in FIGS. 6A and 6B, the core circuitry support structure 600 may include four alignment features 638, 640, 642, and 644. In other embodiments, the core circuitry support structure 600 may include one or two alignment features. In embodiments, the core circuitry support structure 600 may include more than three alignment features. Additionally, as shown in FIGS. 6A and 6B, and in contrast to embodiments described above, the core circuitry support structure 600 does not include retaining clips or a thinned area for an x-ray identification tag. The lack of these features, in embodiments, may facilitate ease of manufacture such as by injection molding.

Embodiments of an IMD having a core circuit support structure configured to receive a hybrid circuit assembly are described above, and include configurations designed to enhance the internal volume of the IMD. FIG. 7 is a flow diagram depicting an illustrative method 700 of manufacturing an IMD in accordance with embodiments of the disclosure. The IMD may be, for example, the IMD 102 depicted in FIG. 1, the IMD 200 depicted in FIGS. 2A-2E, and/or the like.

Embodiments of the method 700 include providing a hybrid circuit assembly (block 702), which may include obtaining and/or assembling one or more portions of a hybrid circuitry assembly such as, for example, by assembling an integrated circuit, coupling circuitry to a printed circuit board (PCB), and/or the like. The method 700 also includes forming a core circuitry support structure (block 704) and coupling the hybrid circuitry assembly to the core circuitry support structure to form a core circuitry assembly (block 706). The core circuitry support structure may be formed using any number of different process such as, for example, stereo lithography, injection molding, additive manufacturing (e.g., 3D printing), and/or the like. Forming the core circuitry assembly may also include coupling a cover to the core circuitry support structure.

The method 700 also may include providing a header (block 708), which may include obtaining and/or assembling one or more portions of a header such as, for example, by arranging circuit components (e.g., an electrode and an antenna) on a scaffold assembly and enclosing the scaffold assembly within a header assembly housing. The method 700 may also include providing a battery assembly (block 710) and providing feed-through assemblies (block 712), which may include obtaining and/or assembling a battery assembly and/or a first and second feed-through assembly.

As depicted in FIG. 7, embodiments of the method 700 also include coupling the feed-through assemblies to the core circuitry assembly (block 714), coupling the header to a first feed-through assembly (block 716), and coupling the battery assembly to a second feed-through assembly (block 718). In embodiments, the method 700 includes forming first and second portions of a core assembly housing (block 720). In embodiments, the core assembly housing portions may be molded, cut, and/or the like, and may be identical or similar to the core assembly housing portions 228 and 230 depicted in FIGS. 2A-2C. As shown in FIG. 7, embodiments of the method 700 also include positioning the core assembly housing portions around the core circuitry assembly (block 722) and welding the core assembly housing portions together (block 724).

Various modifications and additions can be made to the exemplary embodiments discussed without departing from the scope of the disclosed subject matter. For example, while the embodiments described above refer to particular features, the scope of this disclosure also includes embodiments having different combinations of features and embodiments that do not include all of the described features. Accordingly, the scope of the disclosed subject matter is intended to embrace all such alternatives, modifications, and variations as fall within the scope of the claims, together with all equivalents thereof.

We claim:

1. A medical device comprising:
a housing for the medical device;
a printed circuit board (PCB) positioned in the housing and including alignment notches;
a header having a first end and a second end, wherein the header includes a first electrode and an antenna;
a second electrode on an opposite end of the housing from the header;

a feed-through assembly coupled to the second end of the header, wherein the feed-through assembly is electrically coupled between the PCB and the header; and a support structure positioned in the housing and including:

a frame with outer walls that define a cavity, wherein at least a portion of the PCB is positioned within the cavity, and alignment features respectively protruding from the outer walls and through at least a portion of the alignment notches.

2. The medical device of claim 1, wherein the alignment features are positioned at corners of the frame.

3. The medical device of claim 1, wherein the support structure includes exactly four alignment features.

4. The medical device of claim 3, wherein the PCB includes exactly four alignment notches.

5. The medical device of claim 1, wherein the outer walls include:

a first end wall, a second, opposite end wall, and a pair of parallel, opposed side walls, wherein the first end wall, second end wall, and side walls define the cavity.

6. The medical device of claim 5, wherein the first end wall defines a first shelf portion, wherein the second end wall defines a second shelf portion.

7. The medical device of claim 6, wherein the PCB rests on the first shelf portion and the second shelf portion.

8. The medical device of claim 1, wherein at least one of the alignment features is shaped and sized differently than another alignment feature.

9. The medical device of claim 1, further comprising:

a first set of circuitry components coupled to a first surface of the PCB; and a second set of circuitry components coupled to a second surface of the PCB opposite the first surface, wherein the first set of circuitry components extend within the cavity.

10. The medical device of claim 9, wherein the first set of circuitry components includes an antenna or an inductive coil.

11. The medical device of claim 1, wherein the frame is rectangular shaped.

12. The medical device of claim 1, wherein the frame includes spacer arranged and shaped to maintain a position of the frame with respect to the housing.

13. The medical device of claim 1, further including a second feed-through assembly.

14. The medical device of claim 13, wherein the second feed-through assembly is electrically coupled between the PCB and the second electrode.

15. The medical device of claim 14, further including a first conductor coupled between the PCB and the first feed-through assembly, and further including a second conductor coupled between the PCB and the second feed-through assembly.

* * * * *